United States Patent
Jeon et al.

(10) Patent No.: US 11,266,658 B2
(45) Date of Patent: Mar. 8, 2022

(54) PREPARATION, COMPRISING INCLUSION COMPLEX OF VARENICLINE OR PHARMACEUTICALLY ACCEPTABLE SALT THEREOF, FOR ORAL ADMINISTRATION

(71) Applicant: CTC BIO, INC., Seoul (KR)

(72) Inventors: Hong Ryeol Jeon, Gyeonggi-do (KR); Do-Woo Kwon, Chungcheongnam-do (KR); Bong-Sang Lee, Gyeonggi-do (KR); Seul Ki Meang, Seoul (KR); Su-Jun Park, Gyeonggi-do (KR); Seong-Shin Kwak, Gyeonggi-do (KR)

(73) Assignee: CTC BIO, INC., Seoul (KR)

( * ) Notice: Subject to any disclaimer, the term of this patent is extended or adjusted under 35 U.S.C. 154(b) by 7 days.

(21) Appl. No.: 16/488,005

(22) PCT Filed: Mar. 2, 2018

(86) PCT No.: PCT/KR2018/002551
§ 371 (c)(1),
(2) Date: Aug. 22, 2019

(87) PCT Pub. No.: WO2018/160043
PCT Pub. Date: Sep. 7, 2018

(65) Prior Publication Data
US 2020/0061078 A1      Feb. 27, 2020

(30) Foreign Application Priority Data

Mar. 3, 2017 (KR) .................. 10-2017-0027790
Mar. 3, 2017 (KR) .................. 10-2017-0027791

(51) Int. Cl.
| | | |
|---|---|---|
| *A61K 31/495* | (2006.01) |
| *A61K 47/00* | (2006.01) |
| *A61K 9/20* | (2006.01) |
| *A61K 9/14* | (2006.01) |
| *A61K 9/00* | (2006.01) |
| *A61K 31/55* | (2006.01) |
| *A61K 47/69* | (2017.01) |
| *A61K 9/70* | (2006.01) |

(52) U.S. Cl.
CPC ............ *A61K 31/55* (2013.01); *A61K 9/0056* (2013.01); *A61K 9/20* (2013.01); *A61K 9/7007* (2013.01); *A61K 47/6951* (2017.08)

(58) Field of Classification Search
CPC ......... A61K 31/55; A61K 9/7007; A61K 9/00
USPC .................................................. 514/249, 778
See application file for complete search history.

(56) References Cited

U.S. PATENT DOCUMENTS

| | | | | |
|---|---|---|---|---|
| 5,866,179 A | * | 2/1999 | Testa ..................... | A61K 9/0058 424/195.18 |
| 6,410,550 B1 | | 6/2002 | Coe et al. | |
| 2006/0057207 A1 | * | 3/2006 | Ziegler ................ | A61K 9/2054 424/484 |
| 2007/0269386 A1 | | 11/2007 | Steen et al. | |

FOREIGN PATENT DOCUMENTS

| | | |
|---|---|---|
| EP | 2233134 A1 | 9/2010 |
| JP | 2006-528237 A | 12/2006 |
| KR | 10-2004-0079012 A | 9/2004 |
| KR | 10-2009-0033330 A | 4/2009 |
| KR | 10-2011-0071008 A | 6/2011 |
| WO | WO-99/35131 A1 | 7/1999 |
| WO | WO-01/62736 A1 | 8/2001 |
| WO | WO-2004-103372 A1 | 12/2004 |
| WO | WO-2006-040680 A1 | 4/2006 |
| WO | WO-2009-007768 A1 | 1/2009 |
| WO | WO-2009-080021 A1 | 7/2009 |
| WO | WO-2010-044736 A1 | 4/2010 |
| WO | WO-2010-143070 A2 | 12/2010 |

OTHER PUBLICATIONS

International Search Report from corresponding PCT Application No. PCT/KR2018/002551, dated Jul. 6, 2018.
Ebbert, J. O., et al.; "Effect of Varenicline on Smoking Cessation through Smoking Reduction: a Randomized Clinical Trial", Jama, 2015, vol. 313, No. 7, pp. 687-694.
Written Opinion of the International Searching Authority from corresponding PCT Application No. PCT/KR2018/002551, dated Jul. 6, 2018.

* cited by examiner

*Primary Examiner* — Shengjun Wang
(74) *Attorney, Agent, or Firm* — Harness, Dickey & Pierce, P.L.C.

(57) ABSTRACT

The present disclosure relates to an orally administered pharmaceutical formulation containing an inclusion complex formed as varenicline or a pharmaceutically acceptable salt thereof is included in cyclodextrin. The pharmaceutical formulation can improve convenience of medication by effectively masking the bitter taste of the drug and the irritation during swallowing, can provide the oxidation stability of varenicline and can improve the solubility of the drug.

11 Claims, No Drawings

PREPARATION, COMPRISING INCLUSION COMPLEX OF VARENICLINE OR PHARMACEUTICALLY ACCEPTABLE SALT THEREOF, FOR ORAL ADMINISTRATION

CROSS-REFERENCE TO RELATED APPLICATIONS

This application is a national phase application of PCT Application No. PCT/KR2018/002551, filed on Mar. 2, 2018, which claims the benefit and priority to Korean Patent Application Nos. 10-2017-0027790, filed on Mar. 3, 2017 and 10-2017-0027791, filed on Mar. 3, 2017. The entire disclosures of the applications identified in this paragraph are incorporated herein by references.

FIELD

The present disclosure relates to a formulation containing varenicline or a pharmaceutically acceptable salt thereof as an active ingredient, more particularly to an orally administered formulation containing varenicline or a pharmaceutically acceptable salt thereof.

BACKGROUND

Varenicline has the following chemical formula:

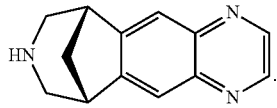

Varenicline is also called 5,8,14-triazatetracyclo [10.3.1.0$^{2,11}$.0$^{4,9}$]-hexadeca-2(11),3,5,7,9-pentane or 7,8,9,10-tetrahydro-6,10-methano-6H-pyrazino[2,3-h][3]-benzazepine. Varenicline and a pharmaceutically acceptable acid addition salt thereof are mentioned in International Patent Publication No. WO1999/35131.

Varenicline binds to the neuronal nicotinic acetylcholine receptor and is useful in regulating cholinergic action. Accordingly, varenicline is useful in treating various conditions or diseases, for example, inflammatory bowel disease (non-limiting examples: ulcerative colitis, pyoderma gangrenosum and Crohn's disease), irritable bowel syndrome, spasmodic dystonia, chronic pain, acute pain, celiac sprue, pouchitis, vasoconstriction, anxiety, panic disorder, depression, bipolar disorder, autism, sleep disorder, jet lag syndrome, amyotrophic lateral sclerosis (ALS), cognitive impairment, hypertension, bulimia, anorexia, obesity, cardiac arrhythmia, gastric acid hypersecretion, ulcer, pheochromocytoma, progressive supranuclear palsy, drug dependence and addiction (dependence on or addiction to, e.g., nicotine (and (or) tobacco products), alcohol, benzodiazepine, barbiturate, opioid or cocaine), headache, migraine, spasm, traumatic brain injury (TBI), obsessive-compulsive disorder (OCD), psychosis, Huntington's chorea, tardive dyskinesia, hyperkinesia, alexia, schizophrenia, multi-infarct dementia, age-related cognitive decline, epilepsy (including absence epilepsy), Alzheimer's disease (AD), Parkinson's disease (PD), attention deficit hyperactivity disorder (ADHD) and Tourette syndrome.

Varenicline tartrate is sold as a 1-mg or 0.5-mg tablet and is used as a smoking cessation aid to treat nicotine addiction or reduce tobacco addiction or consumption.

Varenicline can be administered through various routes. When considering the convenience of carrying and medication, it may be provided specifically as an oral formulation, more specifically an intraoral dispersible formulation. However, varenicline has a characteristic bitter taste and may cause an unpleasant sensation when swallowing. Therefore, it is not easy to be prepared into a formulation for oral administration, particularly an intraoral dispersible formulation whose taste is directly felt during oral administration, e.g., an orally dissolving film, an orally disintegrating tablet, a suspension, a suspension tablet, a rapidly disintegrating tablet, an orally disintegrating capsule, an orally disintegrating granule, an orally disintegrating troche, a sublingual tablet, a powder and/or a chewable tablet. Especially, it is difficult to be used as an active ingredient of an orally administered pharmaceutical formulation for treating a condition or a disease requiring regular medication for a long period of time.

SUMMARY

Technical Problems

The present disclosure is directed to providing a formulation which provides varenicline or a pharmaceutically acceptable salt thereof in the form of an inclusion complex, thereby masking the characteristic bitter taste of varenicline, improving the content uniformity in the formulation and improving the stability of the formulation.

The present disclosure is directed to providing a novel preparation method which can reduce the decrease in varenicline content and the generation of related substances during the preparation of a formulation containing varenicline.

The present disclosure is directed to providing a method capable of improving the stability of an active ingredient.

Technical Solution

In order to solve the technical problems described above, the present disclosure provides an orally administered pharmaceutical formulation, containing an inclusion complex formed as varenicline or a pharmaceutically acceptable salt thereof is included in cyclodextrin, a method for preparing the same and a method for treating by orally administering the same to a subject in need thereof.

Although varenicline or a pharmaceutically acceptable salt thereof is desired to be used as a formulation which is disintegrated quickly in the oral cavity to achieve a quick effect, an excessive amount of flavor or sweetener has to be used due to the characteristic bitter taste of the ingredient and this leads to decreased stability of the formulation. The inventors of the present disclosure have recognized the problem of the characteristic unpleasant state of varenicline in the process of developing an orally administered pharmaceutical formulation containing varenicline or a pharmaceutically acceptable salt thereof and have completed the present disclosure. In addition, the inventors of the present disclosure have identified that the uniformity of drug content and formulation stability may be improved when it is provided as an inclusion complex using cyclodextrin, particularly β-cyclodextrin, and have completed the present disclosure.

The inventors of the present disclosure have also identified that the inclusion complex formed by adding cyclodextrin can improve the stability of varenicline and can reduce related substances.

The cyclodextrin of the present disclosure has been identified to have an excellent ability of forming an inclusion complex and masking the unpleasant taste of varenicline or a pharmaceutically acceptable salt thereof. In particular, it was confirmed that the formulation the present disclosure can mask the unpleasant taste and have improved uniformity of drug content and formulation stability due to the inclusion complex of cyclodextrin. In addition, the present disclosure can provide an orally administered pharmaceutical formulation with improved swallowing.

Cyclodextrin (CD) is a cylindrical compound obtained by cyclizing 6-12 glucose residues obtained from liquefaction of starch with CGTase.

The inventors of the present disclosure have identified that an excellent ability of forming the inclusion complex and effectively masking the unpleasant taste can be achieved by adding cyclodextrin, particularly β-cyclodextrin. Also, they have identified that uniform distribution of the drug in the formulation can be achieved together with excellent film formability as well as adequate hardness.

In the present disclosure, varenicline or a pharmaceutically acceptable salt thereof is used as an active ingredient.

The term 'inclusion complex' used in the present disclosure may be understood as an inclusion compound and refers to a form wherein varenicline or a pharmaceutically acceptable salt thereof is wholly or partly included in a network of cyclodextrin. It is obtained by dissolving cyclodextrin and the drug in an appropriate solvent and conducting reaction for a predetermined time. It can be directly prepared into a formulation in the dissolved state. Alternatively, for use as a dried product, the solvent may be removed through filtering or evaporation under reduced pressure.

In the present disclosure, the 'active ingredient' refers to a therapeutically active compound, any prodrug thereof or a solvate of a pharmaceutically acceptable salt of the compound or the prodrug.

In the present disclosure, the 'ingredient' refers to any substance that constitutes a pharmaceutical formulation with varenicline, a prodrug, a pharmaceutically acceptable salt or a solvate thereof, such as an excipient, a plasticizer, a disintegrant, a diluent, a solvent, a penetration enhancer, a preservative, a buffer, a gelator, a lubricant, a carrier, a stabilizer, a gel, a dye, a pigment, a surfactant, an inert filler, an adhesive, a texturizer, a softener, an emulsifier and a mixture thereof.

In the present disclosure, the 'varenicline' includes the parent drug, a prodrug thereof, a pharmaceutically acceptable salt of the parent drug or the prodrug and a solvate thereof. The parent drug of varenicline is described in International Patent Publication No. WO1999/35131, the disclosures of which are incorporated herein by reference. A method for preparing varenicline is described in U.S. Pat. No. 6,410,550, the disclosures of which are incorporated herein by reference. The resolution of a racemic mixture of varenicline is described in International Patent Publication No. WO2001/62736, the disclosures of which are incorporated herein by reference.

The pharmaceutical formulation according to the present disclosure may contain varenicline or a varenicline derivative instead of or together with it as an active ingredient. Accordingly, the pharmaceutical formulation according to the present disclosure may contain a derivative which has a pharmacological activity comparable to that of varenicline.

In the present disclosure, the term 'pharmaceutically acceptable' means chemical, physical and/or toxicological compatibility with other ingredients constituting a composition and/or a mammal treated with the same.

In the present disclosure, the 'pharmaceutically acceptable salt' refers to a nontoxic acid addition salt derived from an inorganic acid or an organic acid. Suitable acid derivatives include, for example, halide, tosylate, mesylate, thiocyanate, sulfate, bisulfate, sulfite, bisulfite, aryl sulfonate, alkyl sulfate, fumarate, oxalate, phosphonate, phosphate, monohydrogen phosphate, dihydrogen phosphate, metaphosphate, pyrophosphonate, alkanoate, cycloalkyl alkanoate, aryl alkanoate, adipate, alginate, aspartate, benzoate, fumarate, glucoheptanoate, glycerophosphate, lactate, malate, nicotinate, palmitate, pectinate, picrate, pivalate, succinate, tartrate, citrate, camphorate, camphorsulfonate, digluconate, trifluoroacetate, hydrochloride, hydrobromide, salicylate, etc. Any pharmaceutically acceptable salt of varenicline whose stability is decreased by water is included, although not being limited thereto. Specifically, the pharmaceutically acceptable salt of varenicline may be one or more selected from a group consisting of varenicline salicylate, varenicline sulfate, varenicline fumarate, varenicline oxalate, varenicline hydrochloride, varenicline hydrobromide, varenicline citrate, varenicline malate, varenicline succinate, varenicline phosphate, varenicline tosylate, varenicline tartrate and varenicline mesylate. The acid addition salt may be prepared by a common method, for example, by dissolving the compound in an excess amount of an aqueous acid solution and precipitating the salt using a water-miscible organic solvent, e.g., methanol, ethanol, acetone or acetonitrile. After heating an equimolar mixture of the compound and an acid or an alcohol in water, the mixture may be dried through evaporation or the precipitated salt may be filtered through suction.

As the active ingredient of the present disclosure, the varenicline or the pharmaceutically acceptable salt thereof described above may be used without limitation. Specifically, varenicline tartrate, varenicline fumarate, varenicline oxalate, varenicline salicylate, varenicline sulfate, varenicline fumarate, varenicline oxalate, varenicline hydrochloride, varenicline hydrobromide, varenicline citrate, varenicline malate, varenicline succinate, varenicline phosphate, varenicline tosylate or varenicline mesylate may be used. More specifically, varenicline sulfate, varenicline hydrochloride, varenicline salicylate, varenicline tartrate, varenicline hydrobromide or varenicline may be used. Most specifically, varenicline tartrate, varenicline salicylate or a mixture thereof may be used.

The formulation according to an exemplary embodiment of the present disclosure contains an inclusion complex which is formed as the active ingredient is included in cyclodextrin.

The cyclodextrin includes β-cyclodextrin, α-cyclodextrin and γ-cyclodextrin. Specifically, a formulation containing β-cyclodextrin may not only exhibit an excellent effect of masking bitter taste but also help the uniform dispersion of the active ingredient. Also, the formulation prepared using β-cyclodextrin as a taste masking agent may exhibit a quick medicinal effect while providing an excellent effect of masking bitter taste in the oral cavity. In addition, the cyclodextrin may be a derivative containing a hydroxypropyl or methyl group.

In an exemplary embodiment of the present disclosure, the orally administered formulation containing varenicline or a pharmaceutically acceptable salt thereof may contain the varenicline or the pharmaceutically acceptable salt thereof and cyclodextrin at a weight ratio of 20:1 to 1:15,000 (varenicline or pharmaceutically acceptable salt thereof: cyclodextrin), specifically 10:1 to 1:15,000, more specifically 10:1 to 1:10,000, more specifically 10:1 to 1:700, more specifically 2.5:1 to 1:700, more specifically 2:1 to 1:600, more specifically 1.5:1 to 1:150. At this weight ratio, it may exhibit an excellent taste-masking effect, excellent formulation stability and excellent drug dispersibility. In addition, a small amount of sweetener or flavor may be used when the content is in the above range and the preference for the formulation may be improved due to improved swallowing. Also, the disintegration rate in the oral cavity, texture and convenience of medication are superior. In addition, when the content is in the above range, the cyclodextrin remaining after the varenicline-cyclodextrin inclusion complex is formed may be helpful in improving the uniformity of the drug in the formulation.

In particular, the formulation the present disclosure may improve the stability of the drug in the formulation.

The improved stability of the formulation the present disclosure may be understood that the degradation of the varenicline or the pharmaceutically acceptable salt thereof in the formulation by water may be decreased and the generation of related substances may be decreased.

For example, the formulation may be provided as a film formulation. The film formulation may have a weight ratio of the varenicline or the pharmaceutically acceptable salt thereof and cyclodextrin of 2:1 to 1:230 (varenicline or pharmaceutically acceptable salt thereof:cyclodextrin), specifically 1:3.5 to 1:110.

In another exemplary embodiment, the formulation may be provided as a rapidly disintegrating tablet. The rapidly disintegrating tablet may have a weight ratio of the varenicline or the pharmaceutically acceptable salt thereof and cyclodextrin of 1:4 to 1:520 (varenicline or pharmaceutically acceptable salt thereof:cyclodextrin), specifically 1:3.5 to 1:280.

In another exemplary embodiment, a liquid formulation, a suspension formulation, an elixir formulation, a syrup formulation or a lemonade formulation may have a ratio of 2:1 to 1:15000 (varenicline or pharmaceutically acceptable salt thereof:cyclodextrin), specifically 1:1 to 1:2000, and a chewable tablet, a dispersible tablet, a gum formulation, a granule, an effervescent granule, a powder, a buccal tablet or a mucoadhesive tablet may have a ratio of 2:1 to 1:2000, specifically 1:1 to 1:1000.

The ratio is a weight ratio.

The organic acid may be one or more organic acid selected from a group consisting of formic acid, glyoxylic acid, oxalic acid, glycolic acid, acrylic acid, pyruvic acid, malonic acid, propanoic acid, 3-hydrocypropanoic acid, lactic acid, glyceric acid, fumaric acid, maleic acid, oxaloacetic acid, crotonic acid, acetoacetic acid, 2-oxobutanoic acid, methylmalonic acid, succinic acid, malic acid, L-tartaric acid, DL-tartaric acid, meso-tartaric acid, butanoic acid, isobutanoic acid, hydroxybutanoic acid, itaconic acid, mesaconic acid, oxoglutaric acid, glutaric acid, methylsuccinic acid, valeric acid, isovaleric acid, pivalic acid, phenol, cis-aconitic acid, ascorbic acid, citric acid, isocitric acid, adipic acid, caproic acid, benzoic acid, salicylic acid, gentisic acid, protocatechuic acid, gallic acid, cyclohexanecarboxylic acid, pimelic acid, phthalic acid, isophthalic acid, terephthalic acid, phenylacetic acid, toluic acid, m-toluic acid, p-toluic acid, mandelic acid, homogentisic acid, suberic acid, octanoic acid, cinnamic acid, nonanoic acid, oleic acid, acetic acid, hydrochloric acid, boric acid, phosphoric acid and sulfuric acid, specifically one or more organic acid selected from a group consisting of tartaric acid, salicylic acid, benzoic acid, acetic acid and phosphoric acid, more specifically tartaric acid.

The pharmaceutical formulation according to the present disclosure may be prepared as an orally administered formulation. For example, it may be prepared into various formulations, e.g., a tablet, a film, a suspension, a granule, a gel, a pill, a tincture, a decoction, an infusion, a spirit, a fluid extract, an elixir, an extract, a syrup, a powder, an aromatic water, a lemonade, etc. And, the tablet may be prepared into various forms, e.g., an orally disintegrating tablet, a mucoadhesive tablet, a dispersible tablet, a sublingual tablet, a buccal tablet, a chewable tablet, an effervescent tablet, a solution tablet, etc. In addition, those of ordinary skill can make various modifications to the tablet as desired. It may be an intraoral dispersible formulation, e.g., an orally dissolving film, an orally disintegrating tablet, a suspension, a suspension tablet, a rapidly disintegrating tablet, an orally disintegrating granule, an orally disintegrating troche, a sublingual tablet, a powder and/or a chewable tablet. When considering the situation where the pharmaceutical formulation is administered, portability and various purposes, the pharmaceutical formulation according to the present disclosure may be prepared as a suspension formulation, an orally dissolving film formulation, a rapidly disintegrating tablet or an orally disintegrating granule. Specifically, 80% or more of the formulations may be dissolved, dispersed or disintegrated within 10 minutes or 5 minutes after oral administration. The term orally dissolving film may be used interchangeably with a film, a strip, an orally disintegrating film, etc. and refers to a formulation which is adhered in the oral cavity, e.g., on the tongue, on the oral mucosa, below the tongue, etc.

Specifically, an orally dissolving (disintegrating) film, an orally disintegrating tablet, a sublingual tablet, a granule, an effervescent granule, a powder, an internal solution, a troche, an elixir, a syrup, a suspension, an effervescent tablet, a chewable tablet, a solution tablet, a dispersible tablet, a gum, a lemonade, an aromatic water, a spirit, a buccal tablet, a mucoadhesive tablet, an oral patch, etc. may be used. Most specifically, an orally dissolving (disintegrating) film or an orally disintegrating tablet may be used.

When the orally administered pharmaceutical formulation according to the present disclosure is prepared as an orally dissolving film, a polymer has to be contained to form the film. Because the orally administered pharmaceutical formulation according to the present disclosure contains many anionic ingredients, compatibility with the polymer is important. Therefore, pullulan, hydroxypropyl cellulose (HPC), hydroxypropyl methylcellulose (HPMC), polyvinylpyrrolidone (PVP), starch, a polyethylene glycol-polyvinyl alcohol copolymer, copovidone, hydroxyethyl cellulose, hydroxypropyl starch, polyethylene oxide, poloxamer or a mixture thereof may be specifically used. The polymer may be contained in an amount of 20-50 wt % based on the weight of the dried film, although not being limited thereto.

The orally administered pharmaceutical formulation according to the present disclosure may further contain a pharmaceutically acceptable carrier that can be commonly added to a pharmaceutical formulation. The pharmaceutically acceptable carrier may contain an additive commonly used in the pharmaceutical field such as an excipient, a plasticizer, a disintegrant, a diluent, a solvent, a penetration enhancer, a preservative, a buffer, a gelator, a lubricant, a carrier, a stabilizer, a gel, a dye, a pigment, a surfactant, an inert filler, an adhesive, a texturizer, a softener, an emulsifier and a mixture thereof.

The orally administered pharmaceutical formulation according to the present disclosure may contain 40-99.7 wt % of the additive based on the total weight of the formulation. When the pharmaceutical formulation is an orally disintegrating film, it may contain 90-99.8 wt % of the additive based on the total weight of the formulation. When the pharmaceutical formulation is a rapidly disintegrating tablet, it may contain 90-99.8 wt % of the additive based on the total weight of the formulation.

A suitable binder or excipient includes, for example, cellulose, methyl cellulose, ethyl cellulose, hydroxypropyl cellulose, hydroxymethyl cellulose, polypropylpyrrolidone, polyvinylpyrrolidone, gelatin, polyethylene glycol, starch, natural or synthetic gum (e.g., alginate or gum arabic), mannitol, microcrystalline cellulose, anhydrous calcium hydrogen phosphate, sorbitol, L-HPC (low-substituted hydroxypropyl cellulose), pregelatinized starch, lactose or a mixture thereof, although not being limited thereto. Specifically, the binder or excipient may be contained in an amount of 0.01-90 wt % based on the total weight of the orally administered pharmaceutical formulation. When the pharmaceutical formulation is an orally disintegrating film, it may contain 1-90 wt % of the binder or excipient based on the total weight of the pharmaceutical formulation. When the pharmaceutical formulation is a rapidly disintegrating tablet, it may contain 1-99.8 wt % of the binder or excipient based on the total weight of the pharmaceutical formulation.

A suitable lubricant includes, for example, calcium stearate, glyceryl monostearate, glyceryl palmitostearate, magnesium stearate, polyethylene glycol, sodium benzoate, sodium lauryl sulfate, sodium stearyl fumarate, stearic acid, talc and zinc stearate, although not being limited thereto. Specifically, the lubricant may be contained in an amount of 0.1-3 wt % based on the total weight of the orally administered pharmaceutical formulation. When the pharmaceutical formulation is a rapidly disintegrating tablet, it may contain 0.1-5 wt % of the lubricant based on the total weight of the pharmaceutical formulation.

A suitable disintegrant includes, for example, sodium starch glycolate, sodium carboxymethyl cellulose, calcium carboxymethyl cellulose, croscarmellose sodium, polyvinylpyrrolidone, methyl cellulose, microcrystalline cellulose, powdered cellulose, lower alkyl-substituted hydroxypropyl cellulose, polacrilin potassium, starch, pregelatinized starch, sodium alginate, etc., although not being limited thereto. Specifically, the disintegrant may be contained in an amount of 1-80 wt % based on the total weight of the orally administered pharmaceutical formulation. When the pharmaceutical formulation is an orally disintegrating film, it may contain 3-45 wt % of the disintegrant based on the total weight of the pharmaceutical formulation. When the pharmaceutical formulation is a rapidly disintegrating tablet, it may contain 0.1-90 wt % of the disintegrant based on the total weight of the pharmaceutical formulation.

If necessary, a sweetener, a flavor and/or a colorant may be further contained, but the sweetener, flavor and/or colorant may cause irritation during swallowing. The sweetener, flavor and/or colorant may be contained in an amount of 5 wt % or less, more specifically 3 wt % or less, most specifically 1 wt % or less, based on the total weight of the orally administered pharmaceutical formulation according to the present disclosure.

When the pharmaceutical formulation of the present disclosure is used to treat dependence on or addiction to nicotine or tobacco products or as a smoking cessation aid, it may further contain, in addition to the varenicline or the pharmaceutically acceptable salt thereof, another drug as an active ingredient as long as the purpose of the present disclosure is not negatively affected. For example, it may contain one or more selected from a group consisting of an α7-nicotinic acetylcholine receptor antagonist, an agent for treating withdrawal symptoms (e.g., bupropion, rimonabant, dihydroderisodin, dopamine, mecamylamine, cytisine, 3-methylaminoisocamphene, baclofen, clopazolin, butanone, etc.), a nicotine-specific antibody, an anti-protein antibody, a natural product (e.g., angelicae radix, zizyphus seed, red ginseng, skullcap, etc.) or a combination thereof. Those of ordinary skill can select various drugs in addition to the above-described drugs, if necessary.

The pharmaceutical formulation according to the present disclosure may be used for any disease, disorder and/or symptom treated by administering the varenicline or the pharmaceutically acceptable salt thereof as an active ingredient without limitation. For example, it may be used for a disorder or disease including inflammatory bowel disease, ulcerative colitis, pyoderma gangrenosum, Crohn's disease, irritable bowel syndrome, spasmodic dystonia, chronic pain, acute pain, celiac sprue, pouchitis, vasoconstriction, anxiety, panic disorder, depression, bipolar disorder, autism, sleep disorder, jet lag syndrome, amyotrophic lateral sclerosis (ALS), cognitive impairment, hypertension, bulimia, anorexia, obesity, cardiac arrhythmia, gastric acid hypersecretion, ulcer, pheochromocytoma, progressive supranuclear palsy, drug dependence and addiction (dependence on or addiction to, e.g., nicotine, tobacco products, alcohol, benzodiazepine, barbiturate, opioid or cocaine), headache, apoplexy, traumatic brain injury (TBI), obsessive-compulsive disorder (OCD), psychosis, Huntington's chorea, tardive dyskinesia, hyperkinesia, alexia, schizophrenia, multi-infarct dementia, age-related cognitive decline, epilepsy (including absence epilepsy), Alzheimer's disease (AD), Parkinson's disease (PD), attention deficit hyperactivity disorder (ADHD), Tourette syndrome and other similar disorders or diseases known in the art (although not being limited thereto). Specifically, it may be used to treat dependence on or addiction to nicotine or tobacco products.

In the present disclosure, the 'treatment' means any action of improving or beneficially altering an (acute or chronic) disease, a disorder or a symptom resulting therefrom by administering the pharmaceutical formulation. In a broad sense, the 'treatment' includes 'prevention', which means any action of preventing the occurrence of a disease or a symptom resulting therefrom or delaying the occurrence by administering the pharmaceutical formulation. The 'treatment' includes, for example, the interruption, alleviation, improvement, stopping, suppression, delaying, reversal, etc. of an (acute or chronic) disease, a disorder or a symptom resulting therefrom.

The dosage, frequency and continuance of administration will vary depending on such factors as the characteristics and seriousness of the condition to be treated, the age and general physical conditions of a subject and the resistance of the subject to the active ingredient. The pharmaceutical formulation may be provided as a once-daily administration form, a multiple-daily administration form or a once-weekly administration form. The prescription may last from about 2-3 days to several weeks or longer.

In an exemplary embodiment, the pharmaceutical formulation according to the present disclosure may contain 0.5-1 mg of the varenicline or the pharmaceutically acceptable salt thereof for a single-dose unit.

In another exemplary embodiment, the present disclosure provides a method for preparing an orally administered formulation of varenicline or a pharmaceutically acceptable salt thereof.

The preparation method includes a process of forming an inclusion complex of varenicline or a pharmaceutically acceptable salt thereof and cyclodextrin.

In an exemplary embodiment, the present disclosure provides a method for preparing an orally administered formulation of varenicline or a pharmaceutically acceptable salt thereof, including:

(S1) a step of preparing a mixture of varenicline or a pharmaceutically acceptable salt thereof and a solvent;

(S2) a step of forming a mixture containing a cyclodextrin inclusion complex by adding cyclodextrin to the mixture and forming a cyclodextrin inclusion complex by heating and stirring the same;

(S3) a step of preparing solution for preparing a formulation by mixing a pharmaceutically acceptable additive in the mixture containing the cyclodextrin inclusion complex; and (S4) a step of preparing the solution for preparing a formulation into the formulation.

Specifically, in the step (S1), the mixture may be formed by mixing varenicline or a pharmaceutically acceptable salt thereof with a solvent which is water, ethanol or a mixture thereof.

Specifically, in the step (S2), cyclodextrin may be added to the mixture of the solvent and the varenicline or the pharmaceutically acceptable salt thereof. During the mixing, stirring may be conducted to form the inclusion complex of the cyclodextrin and the varenicline or the pharmaceutically acceptable salt thereof. More specifically, the stirring during the mixing may be conducted simultaneously with or after the heating.

The heating may be performed at 50-80° C., specifically at 55-75° C. The stirring may be performed for 20 minutes or longer or 30 minutes or longer, specifically for 1 hour or longer.

Specifically, in the step (S3), the solution for preparing a formulation may be prepared by adding a pharmaceutically acceptable additive to the mixture containing the cyclodextrin inclusion complex. The mixture may contain the cyclodextrin inclusion complex and cyclodextrin, which does not form the inclusion complex with the varenicline, may remain. The pharmaceutically acceptable additive that may be contained in the mixture may include a plasticizer, a diluent, a solvent, a preservative, a buffer, a lubricant, a stabilizer, a filler, a softener, a flavor, a colorant, a sweetener, a surfactant, etc., which are commonly used in the art to prepare a formulation.

Specifically, in the step the step (S2), the cyclodextrin inclusion complex may be formed by using an organic acid during the stirring. Specifically, the organic acid may be one or more selected from a group consisting of tartaric acid, salicylic acid, benzoic acid, acetic acid and phosphoric acid. Specifically, in the step (S2), the inclusion complex of the varenicline or the pharmaceutically acceptable salt thereof and the cyclodextrin may be formed by stirring at pH 2.5-5.5, specifically at pH 2.8-4.5.

In an exemplary embodiment, the present disclosure provides a film formulation containing varenicline or a pharmaceutically acceptable salt thereof. The film may be prepared by, in the step (S4), homogenizing a film-forming polymer, a plasticizer, a sweetener, a flavor and the mixture of the inclusion complex and the pharmaceutically acceptable additive and then drying the same. For example, the homogenization may be performed using a homogenizer (Ultra-Turrax T-25, IKA) after adding glycerin, sucralose, ferric oxide red, $TiO_2$ and peppermint and then dissolving or dispersing the same by stirring. Then, after adding a polymer (pullulan) and homogenizing using the same homogenizer, a gas may be removed from the solution for preparing a film in vacuo and the solution may be coated on a support film to an appropriate thickness. Then, the film formulation containing varenicline tartrate may be prepared by drying the same at 60-80° C.

As the support film, a plastic film commonly used in the art to prepare an orally disintegrating film, e.g., a polyethylene terephthalate (PET) film, etc., may be used, although not being limited thereto.

The drying may be performed until the weight of the finally obtained orally disintegrating film is decreased by 5-15 wt %, specifically 7-12 wt %.

In the step (S2), the inclusion complex of the varenicline or the pharmaceutically acceptable salt thereof and the cyclodextrin may be formed by mixing the varenicline or the pharmaceutically acceptable salt thereof and the cyclodextrin at a weight ratio of 2:1 to 1:230 (varenicline or pharmaceutically acceptable salt thereof:cyclodextrin) at pH 2.5-5.5 by adding the organic acid.

The present disclosure may provide a smoking cessation aid containing an inclusion complex wherein varenicline or a pharmaceutically acceptable salt thereof is included in cyclodextrin Advantageous Effects A formulation of the present disclosure can mask the characteristic unpleasant taste of varenicline while improving swallowing of the drug.

The formulation the present disclosure can improve the content uniformity of the drug because the drug is uniformly dispersed in the formulation.

The formulation the present disclosure may have excellent formulation stability and degradation by water may be decreased.

DETAILED DESCRIPTION

Hereinafter, the present disclosure will be explained in detail with reference to Examples. The following examples may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art.

Example 1. Preparation of Film Containing Salt of Varenicline as Active Ingredient (1) Preparation of Film Formulation with Bitter Taste of Varenicline Tartrate Masked A film formulation containing varenicline tartrate as an active ingredient was prepared using the ingredients described in Table 1 by the method described below and the taste-masking effect and physical properties of the film depending on the addition ratio of β-CD and the drug was investigated.

TABLE 1

| | Comparative example 1 | Example (mg/unit) | | | | | | | |
|---|---|---|---|---|---|---|---|---|---|
| | | 1 | 2 | 3 | 4 | 5 | 6 | 7 | 8 |
| API : TM agent | | 10:1 | 2:1 | 1:4 | 1:20 | 1:50 | 1:100 | 1:200 | 1:500 |
| Varenicline Tartrate | 0.85 (0.5 mg as varenicline) | | | | | | | | |
| Beta-Cyclodextrin | | 0.05 | 0.25 | 2.00 | 10.00 | 25.00 | 50.00 | 100.00 | 250.00 |
| Excipients (%) | | | | | | | | | |
| Pullulan | 50.0 | | | | | | | | |
| Glycerin | 12.0 | | | | | | | | |
| Sucralose | 3.0 | | | | | | | | |
| Ferric oxide red | 2.0 | | | | | | | | |
| TiO$_2$ | 10.0 | | | | | | | | |
| Peppermint powder | 3.0 | | | | | | | | |
| Water | q.s. | | | | | | | | |

After adding β-cyclodextrin to a liquid varenicline tartrate solution, the mixture was stirred for 1 hour or longer while heating to 60-70° C. Then, after adding glycerin, sucralose, ferric oxide red, TiO$_2$ and peppermint to purified water and then dissolving or dispersing by stirring, the mixture was homogenized using a homogenizer (Ultra-Turrax T-25, IKA). Then, after adding a polymer (pullulan) and then homogenizing using the same homogenizer, a gas was removed from the solution for preparing a film in vacuo and the solution was coated on a PET film to an appropriate thickness. Then, a film formulation containing varenicline tartrate was prepared by drying the same at 60-80° C.

(2) Preparation of Film Formulation with Bitter Taste of Varenicline Salicylate Masked A film formulation containing varenicline salicylate as an active ingredient was prepared using the ingredients described in Table 2 by the method described below and the taste-masking effect and physical properties of the film depending on the addition ratio of β-CD and the drug was investigated.

TABLE 2

| | Comparative example 2 | Example (mg/unit) | | | | | | | |
|---|---|---|---|---|---|---|---|---|---|
| | | 9 | 10 | 11 | 12 | 13 | 14 | 15 | 16 |
| API : TM agent | | 10:1 | 2:1 | 1:4 | 1:20 | 1:50 | 1:100 | 1:200 | 1:500 |
| Varenicline Salicylate | 0.82 (0.5 mg as varenicline) | | | | | | | | |
| Beta-Cyclodextrin | | 0.05 | 0.25 | 2.00 | 10.00 | 25.00 | 50.00 | 100.00 | 250.00 |
| Excipients (%) | | | | | | | | | |
| Pullulan | 50.0 | | | | | | | | |
| Glycerin | 12.0 | | | | | | | | |
| Sucralose | 3.0 | | | | | | | | |
| Ferric oxide red | 2.0 | | | | | | | | |
| TiO$_2$ | 10.0 | | | | | | | | |
| Peppermint powder | 3.0 | | | | | | | | |
| Water | q.s. | | | | | | | | |

After adding β-cyclodextrin to a liquid varenicline salicylate solution, the mixture was stirred for 1 hour or longer while heating to 60-70° C. Then, after adding glycerin, sucralose, ferric oxide red, TiO$_2$ and peppermint powder to purified water and then dissolving or dispersing by stirring, the mixture was homogenized using a homogenizer (Ultra-Turrax T-25, IKA). Then, after adding a polymer (pullulan) and then homogenizing using the same homogenizer, a gas was removed from the solution for preparing a film in vacuo and the solution was coated on a PET film to an appropriate thickness. Then, a film formulation containing varenicline salicylate was prepared by drying the same at 60-80° C.

(3) Investigation of Taste-Masking Effect and Physical Properties of Film Depending on Addition Ratio of β-CD and Drug The following experiment was conducted to investigate the taste-masking effect and physical properties of the film depending on the addition ratio of β-CD and the drug and the result is given in Table 6.

The taste-masking effect of the film formulation was investigated as follows. The TM sensory test was performed with the formulation of the same amount. A test subject put the formulation sample containing varenicline tartrate of the same amount in the mouth, dissolved it for the same time period, spitted it out and then lightly rinsed the mouth with the same amount of water. Then, the time for which unpleasant taste was maintained was recorded. The time between tests for each formulation sample was set to 3 hours or longer and the subject who felt unpleasant taste longer than 3 hours was excluded from the next test. The detailed evaluation criteria were as follows.

TABLE 3

| | |
|---|---|
| 1-poor | Retention time of unpleasant taste: NLT 60 min. |
| 2-not good | Retention time of unpleasant taste: NLT 20 min. |
| 3-not bad | Retention time of unpleasant taste: NMT 20 min. |
| 4-excellent | Retention time of unpleasant taste: NMT 5 min. |

(NLT: no less than, NMT: no more than)

Tensile strength was tested by the following method. After coating the solution for forming a film on a support film and cutting to a predetermined size, the formed film was detached from the support film and tensile strength was measured using a universal testing machine (texture analyzer) under the following condition.

- Universal testing machine: LLOYS LS-1
- Load cell (N): 100 N
- Grips: Pneumatic vice grips
- Testing speed (mm/min): 200
- Distance between grips (mm): 2
- Air pressure of grip: (MPa): 0

The tensile strength was calculated from the measurement results according to the following equation.

Tensile strength=load value $(N)$/sample area $(mm^2)$

TABLE 4

| | |
|---|---|
| 1-poor | Tensile strength value: NMT 5 N/mm² |
| 2-not good | Tensile strength value: NMT 10 N/mm² |
| 3-not bad | Tensile strength value: NLT 10 N/mm² |
| 4-excellent | Tensile strength value: NLT 15 N/mm² |

Flexibility was evaluated as follows. After coating the solution for forming a film on a support film and cutting to a predetermined size, the formed film was detached from the support film. After folding the formed film, the maximum angle at which the film was not broken was measured.

TABLE 5

| | |
|---|---|
| 1-poor | Maximum folding angle without breaking NMT 60° |
| 2-not good | Maximum folding angle without breaking NMT 90° |
| 3-not bad | Maximum folding angle without breaking: NLT 90° |
| 4-excellent | Maximum folding angle without breaking: NLT 150° |

The measurement result is as follows.

TABLE 6

| Evaluation parameter | Weigh | Comparative Example 1 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| | | | Score = Each parameter value × Weigh | | | | | | | | | | | | | | | |
| Effect of taste masking | 3 | 3 | 3 | 6 | 9 | 9 | 9 | 9 | 9 | 9 | 3 | 3 | 6 | 9 | 9 | 9 | 9 | 9 |
| Tensile strength | 1 | 4 | 4 | 4 | 4 | 4 | 4 | 4 | 3 | 1 | 4 | 4 | 4 | 4 | 4 | 4 | 3 | 1 |
| Flexibility | 1 | 4 | 4 | 4 | 4 | 4 | 4 | 4 | 3 | 2 | 4 | 4 | 4 | 4 | 4 | 4 | 3 | 2 |
| Total score | | 11 | 11 | 14 | 17 | 17 | 17 | 17 | 15 | 12 | 11 | 11 | 14 | 17 | 17 | 17 | 15 | 12 |

As can be seen from Table 6, the taste-masking effect was different depending on the ratio of the varenicline salt and the β-cyclodextrin. The best taste-masking effect was achieved when the β-cyclodextrin was added at a ratio of 1:4 or higher. When the mixing ratio was 1:500 or higher, the addition of the β-cyclodextrin negatively affected the flexibility and tensile strength of the film.

In Table 6, 'weigh' refers to the weight applied to each parameter value. To take Comparative Example 1 for example, the weight 3 was applied to the taste masking value-1 (poor) [1 (taste masking value)*3 (weigh)=3].

Example 2. Preparation of Rapidly Disintegrating Tablet Containing Salt of Varenicline as Active Ingredient (1) Preparation of Rapidly Disintegrating Tablet with Bitter Taste of Varenicline Tartrate Masked A rapidly disintegrating tablet containing varenicline tartrate as an active ingredient was prepared using the ingredients described in Table 7 by the method described below and the taste-masking effect and hardness of the tablet depending on the addition ratio of β-CD and the drug was investigated.

After adding β-CD to a liquid varenicline tartrate solution, the mixture was stirred for 1 hour or longer.

Then, a solid was obtained from the mixture through filtration or evaporation of the solvent under reduced pressure. After adding a binder, a disintegrant, an excipient and a lubricant to the obtained solid and then mixing the same, a tablet was prepared using a tablet-making machine.

TABLE 7

| | Comparative example | Example (mg/unit) | | | | | | | | |
|---|---|---|---|---|---|---|---|---|---|---|
| | 2-1 | 2-1 | 2-2 | 2-3 | 2-4 | 2-5 | 2-6 | 2-7 | 2-8 | 2-9 |
| API : TM agent | 10:1 | 2:1 | 1:4 | 1:20 | 1:50 | 1:100 | 1:250 | 1:500 | 1:1000 | |
| Varenicline Tartrate | 0.85 (0.5 mg as varenicline) | | | | | | | | | |
| Beta-Cyclodextrin | 0.05 | 0.25 | 2.00 | 10.00 | 25.00 | 50.00 | 125.00 | 250.00 | 500.00 | |
| Excipients (%) | | | | | | | | | | |
| Mannitol | 30.0 | | | | | | | | | |
| Avicell | 10.0 | | | | | | | | | |
| HPC-L | 3.0 | | | | | | | | | |
| Magnesium stearate | 0.5 | | | | | | | | | |
| Sucralose | 2.0 | | | | | | | | | |
| Peppermint powder | 2.0 | | | | | | | | | |
| Water | q.s. | | | | | | | | | |

(2) Preparation of Rapidly Disintegrating Tablet with Bitter Taste of Varenicline Salicylate Masked A rapidly disintegrating tablet containing varenicline salicylate as an active ingredient was prepared using the ingredients described in Table 8 by the method described below and the taste-masking effect and hardness of the tablet depending on the addition ratio of β-CD and the drug was investigated.

After adding β-CD to a liquid varenicline salicylate solution, the mixture was stirred for 1 hour or longer.

Then, a solid was obtained from the mixture through filtration or evaporation of the solvent under reduced pressure. After adding a binder, a disintegrant, an excipient and a lubricant to the obtained solid and then mixing the same, a tablet was prepared using a tablet-making machine.

TABLE 8

|  | Comparative example | Example (mg/unit) | | | | | | | | |
| --- | --- | --- | --- | --- | --- | --- | --- | --- | --- | --- |
|  | 2-2 | 2-10 | 2-11 | 2-12 | 2-13 | 2-14 | 2-15 | 2-16 | 2-17 | 2-18 |
| API : TM agent |  | 10:1 | 2:1 | 1:4 | 1:20 | 1:50 | 1:100 | 1:250 | 1:500 | 1:1000 |
| Varenicline Salicylate |  | 0.82 (0.5 mg as varenicline) | | | | | | | | |
| Beta-Cyclodextrin |  | 0.05 | 0.25 | 2.00 | 10.00 | 25.00 | 50.00 | 125.00 | 250.00 | 500.00 |
| Excipients (%) | | | | | | | | | | |
| Mannitol | 30.0 | | | | | | | | | |
| Avicell | 10.0 | | | | | | | | | |
| HPC-L | 3.0 | | | | | | | | | |
| Magnesium stearate | 0.5 | | | | | | | | | |
| Sucralose | 2.0 | | | | | | | | | |
| Peppermint powder | 2.0 | | | | | | | | | |
| Water | q.s. | | | | | | | | | |

(3) Investigation of Taste-Masking Effect and Formability of Rapidly Disintegrating Tablet Depending on Addition Rate of β-CD and Drug The following experiment was conducted to investigate the taste-masking effect and formability of the tablet depending on the addition rate of the β-CD and the drug. The result is given in Table 9.

The taste-masking effect of the tablet was measured in the same manner as the measurement of the taste-masking effect of the film.

The tablet formability was measured based on the hardness of the tablet. The evaluation criteria were as follows.

The hardness was measured using a tablet harness tester (Vankel VK 200). While gradually increasing the force applied to the tablet, the force at the time when the tablet was broken was recorded.

TABLE 9

| 1-poor | Tablet not formed |
| --- | --- |
| 2-not good | Hardness: NMT 3 |
| 3-not bad | Hardness: 3-10 |
| 4-excellent | Hardness: NLT 10 |

The result is as follows.

TABLE 10

|  |  | Comparative example | Example No. | | | | | | | | |
| --- | --- | --- | --- | --- | --- | --- | --- | --- | --- | --- | --- |
|  |  | 2-1 | 2-1 | 2-2 | 2-3 | 2-4 | 2-5 | 2-6 | 2-7 | 2-8 | 2-9 |
| Evaluation parameter | Weigh | | Score = Each parameter value × Weigh | | | | | | | | |
| Effect of taste masking | 3 | 3 | 3 | 6 | 9 | 9 | 9 | 9 | 9 | 9 | 9 |
| Hardness | 1 | 4 | 4 | 4 | 4 | 4 | 4 | 4 | 4 | 3 | 1 |
| Total score |  | 7 | 7 | 10 | 13 | 13 | 13 | 13 | 13 | 12 | 10 |

TABLE 10-continued

| Evaluation parameter | Weigh | Comparative example 2-2 | 2-10 | 2-11 | 2-12 | 2-13 | 2-14 | 2-15 | 2-16 | 2-17 | 2-18 |
|---|---|---|---|---|---|---|---|---|---|---|---|
| | | | Score = Each parameter value × Weigh | | | | | | | | |
| Effect of taste masking | 3 | 3 | 3 | 6 | 9 | 9 | 9 | 9 | 9 | 9 | 9 |
| Hardness | 1 | 4 | 4 | 4 | 4 | 4 | 4 | 4 | 4 | 3 | 1 |
| Total score | | 7 | 7 | 10 | 13 | 13 | 13 | 13 | 13 | 12 | 10 |

As can be seen from Table 10, the taste-masking effect was different depending on the ratio of the varenicline salt and the β-cyclodextrin. The best taste-masking effect was achieved when the β-cyclodextrin was added at a ratio of 1:4 or higher. When the addition amount of the β-cyclodextrin was 1:1000 or higher, the hardness of the prepared orally disintegrating tablet was decreased.

Example 3. Preparation of Suspension Formulation Containing Salt of Varenicline as Active Ingredient 1) After adding β-cyclodextrin to a liquid varenicline tartrate solution, the mixture was stirred for 1 hour or longer while heating to 60-70° C.

2) Then, after adding a flavor, a colorant, a stabilizer, a preservative, a buffer or an excipient to purified water, a suspension formulation was prepared by dissolving or mixing the same through stirring.

TABLE 11

| | Comparative Example 3-1 | Examples (mg/unit) 3-1 | 3-2 | 3-3 | 3-4 | 3-5 | 3-6 | 3-7 | 3-8 | 3-9 |
|---|---|---|---|---|---|---|---|---|---|---|
| API: TM agent | — | 10:1 | 2:1 | 1:4 | 1:20 | 1:50 | 1:100 | 1:250 | 1:500 | 1:1000 |
| Varenicline Tartrate | | 0.85 (0.5 mg as varenicline) | | | | | | | | |
| Beta-Cyclodextrin | — | 0.05 | 0.25 | 2.00 | 10.00 | 25.00 | 50.00 | 125.00 | 250.00 | 500.00 |
| Excipients (%) | | | | | | | | | | |
| Sucralose | | 3 | | | | | | | | |
| Mannitol | | 15 | | | | | | | | |
| Xanthan gum | | 0.1 | | | | | | | | |
| Sodium CMC | | 5.0 | | | | | | | | |
| Propyl paraben | | 0.02 | | | | | | | | |
| Methyl paraben | | 0.08 | | | | | | | | |
| Peppermint powder | | 3.0 | | | | | | | | |
| Water | | q.s. | | | | | | | | |

| Evaluation parameter | Comparative Example 3-1 | Examples No. 3-1 | 3-2 | 3-3 | 3-4 | 3-5 | 3-6 | 3-7 | 3-8 | 3-9 |
|---|---|---|---|---|---|---|---|---|---|---|
| | | Score = Each parameter value × Weigh | | | | | | | | |
| Effect of taste masking | 3 | 3 | 6 | 9 | 9 | 9 | 9 | 9 | 9 | 9 |

Example 4. Preparation of Granule Containing Salt of Varenicline as Active Ingredient 1) After adding β-cyclodextrin to a liquid varenicline tartrate solution, the mixture was stirred for 1 hour or longer while heating to 60-70° C.

2) Then, a solid was obtained by precipitating the solution, followed by filtering and drying. Separately from this, a solution containing a binder, a disintegrant and an excipient (diluent) was prepared and the obtained solid was added into a fluidized-bed granulator and then spry-dried to prepare a granule.

TABLE 12

| | Comparative Example | Examples (mg/unit) | | | | | | | | |
|---|---|---|---|---|---|---|---|---|---|---|
| | 4-1 | 4-1 | 4-2 | 4-3 | 4-4 | 4-5 | 4-6 | 4-7 | 4-8 | 4-9 |
| API: TM agent | — | 10:1 | 2:1 | 1:4 | 1:20 | 1:50 | 1:100 | 1:250 | 1:500 | 1:1000 |
| Varenicline Tartrate | | 0.85 (0.5 mg as varenicline) | | | | | | | | |
| Beta-Cyclodextrin | — | 0.05 | 0.25 | 2.00 | 10.00 | 25.00 | 50.00 | 125.00 | 250.00 | 500.00 |
| Excipients (%) | | | | | | | | | | |
| MCC | | | | | 10 | | | | | |
| Mannitol 160C | | | | | 35 | | | | | |
| HPC-SL | | | | | 2 | | | | | |
| Peppermint powder | | | | | 3.0 | | | | | |
| Sucralose | | | | | q.s. | | | | | |
| Water | | | | | q.s. | | | | | |

| | Comparative Example | Examples No. | | | | | | | | |
|---|---|---|---|---|---|---|---|---|---|---|
| Evaluation parameter | 4-1 | 4-1 | 4-2 | 4-3 | 4-4 | 4-5 | 4-6 | 4-7 | 4-8 | 4-9 |
| | | Score = Each parameter value × Weigh | | | | | | | | |
| Effect of taste masking | 3 | 3 | 6 | 9 | 9 | 9 | 9 | 9 | 9 | 9 |

Also for Examples 3 and 4, taste-masking effect could be achieved by adding the β-cyclodextrin.

Example 5. Investigation of Effect of Adding Acidifier (1) Film Formulation Containing Varenicline Salt A film formulation was prepared in the same manner as in Example 1 under an acidic condition by adding an acidifier as described in Tables 13 and 14. Then, taste-masking effect and film formability were measured. Table 13 shows the composition of a film formulation containing varenicline tartrate and Table 14 shows the composition of a film formulation containing varenicline salicylate.

Preparation method: After dissolving varenicline tartrate or salicylate and β-cyclodextrin in water, the mixture was stirred for 1 hour while heating to 60-70° C. Then, after adding glycerin, sucralose, a sweetener and a flavor, the mixture was dissolved by stirring and then homogenized using a homogenizer (Ultra-Turrax T-24, IKA). Then, after adding pullulan as a film-forming agent and then homogenizing using the same homogenizer, a diluted acidifier solution (tartaric acid 5 mg/mL) was added to the solution for preparing a film little by little until the pH described in Tables 13 and 14 was reached. After removing a gas from the solution in vacuo, the solution was coated on a PET film to an appropriate thickness. Then, a film formulation containing the varenicline salt was prepared by drying the same at 60-80° C.

TABLE 13

| | Comparative Example | | | | | | Examples (mg/mL) | | | | | |
|---|---|---|---|---|---|---|---|---|---|---|---|---|
| | 5-1 | 5-2 | 5-3 | 5-4 | 5-5 | 5-6 | 5-1 | 5-2 | 5-3 | 5-4 | 5-5 | 5-6 |
| Controlled pH | Not controlled | | pH 2 (± 10%) | | pH 6 (± 10%) | | pH 3 (± 10%) | | pH 4 (± 10%) | | pH 5 (± 10%) | |
| API: TM agent | 1:4 | 1:100 | 1:4 | 1:100 | 1:4 | 1:100 | 1:4 | 1:100 | 1:4 | 1:100 | 1:4 | 1:100 |
| Varenicline Tartrate | 0.85 (0.5 mg as varenicline) | | | | | | | | | | | |
| Beta-Cyclodextrin | 2 | 50 | 2 | 50 | 2 | 50 | 2 | 50 | 2 | 50 | 2 | 50 |

| Excipients (%) | |
|---|---|
| Pullulan | 50.0 |
| Glycerin | 12.0 |
| Sucralose | 3.0 |
| Ferric oxide red | 2.0 |
| TiO$_2$ | 10.0 |
| Peppermint powder | 3.0 |
| pH control agent (Tartaric acid) | q.s. |
| Water | q.s. |

| | | Comparative Example | | | | | | Examples No. | | | | | |
|---|---|---|---|---|---|---|---|---|---|---|---|---|---|
| Evaluation parameter | Weigh | 5-1 | 5-2 | 5-3 | 5-4 | 5-5 | 5-6 | 5-1 | 5-2 | 5-3 | 5-4 | 5-5 | 5-6 |
| | | Score = Each parameter value × Weigh | | | | | | | | | | | |
| Effect of taste masking | 3 | 9 | 9 | 9 | 9 | 9 | 9 | 12 | 12 | 12 | 12 | 12 | 12 |
| Film Forming | 1 | 4 | 4 | 4 | 4 | 4 | 4 | 4 | 4 | 4 | 4 | 4 | 4 |
| Total score | | 13 | 13 | 13 | 13 | 13 | 13 | 16 | 16 | 16 | 16 | 16 | 16 |

TABLE 14

| | Comparative Example | | | | | | Examples (mg/mL) | | | | | |
|---|---|---|---|---|---|---|---|---|---|---|---|---|
| | 5-7 | 5-8 | 5-9 | 5-10 | 5-11 | 5-12 | 5-7 | 5-8 | 5-9 | 5-10 | 5-11 | 5-12 |
| Controlled pH | Not controlled | | pH 2 (± 10%) | | pH 6 (± 10%) | | pH 3 (± 10%) | | pH 4 (± 10%) | | pH 5 (± 10%) | |
| API: TM agent | 1:4 | 1:100 | 1:4 | 1:100 | 1:4 | 1:100 | 1:4 | 1:100 | 1:4 | 1:100 | 1:4 | 1:100 |
| Varenicline Salicylate | 0.82 (0.5 mg as varenicline) | | | | | | | | | | | |
| Beta-Cyclodextrin | 2 | 50 | 2 | 50 | 2 | 50 | 2 | 50 | 2 | 50 | 2 | 50 |

| Excipients (%) | |
|---|---|
| Pullulan | 50.0 |
| Glycerin | 12.0 |
| Sucralose | 3.0 |
| Ferric oxide red | 2.0 |
| TiO$_2$ | 10.0 |
| Peppermint powder | 3.0 |
| pH control agent (Tartaric acid) | q.s. |
| Water | q.s. |

| | | Comparative Example | | | | | | Examples No. | | | | | |
|---|---|---|---|---|---|---|---|---|---|---|---|---|---|
| Evaluation parameter | Weigh | 5-7 | 5-8 | 5-9 | 5-10 | 5-11 | 5-12 | 5-7 | 5-8 | 5-9 | 5-10 | 5-11 | 5-12 |
| | | Score = Each parameter value × Weigh | | | | | | | | | | | |
| Effect of taste masking | 3 | 9 | 9 | 9 | 9 | 9 | 9 | 12 | 12 | 12 | 12 | 12 | 12 |
| Film Forming | 1 | 4 | 4 | 4 | 4 | 4 | 4 | 4 | 4 | 4 | 4 | 4 | 4 |
| Total score | | 13 | 13 | 13 | 13 | 13 | 13 | 16 | 16 | 16 | 16 | 16 | 16 |

Film formability was evaluated according to the following criteria.

TABLE 15

| | |
|---|---|
| 1-poor | Film is not formed |
| 2-not good | Formed, but having lots of cracks |
| 3-not bad | Formed, but a little crack |
| 4-excellent | Film is formed well |

(2) Rapidly Disintegrating Tablet Containing Varenicline Salt

A tablet was prepared in the same manner as in Example 2 under an acidic condition by adding an acidifier as described in Tables 16 and 17. Then, taste-masking effect and film formability were measured. Table 16 shows the composition of a rapidly disintegrating tablet containing varenicline tartrate and Table 17 shows the composition of a rapidly disintegrating tablet containing varenicline salicylate.

TABLE 16

| | Comparative Example | | | | | | Examples (mg/unit) | | | | | |
|---|---|---|---|---|---|---|---|---|---|---|---|---|
| | 6-1 | 6-2 | 6-3 | 6-4 | 6-5 | 6-6 | 6-1 | 6-2 | 6-3 | 6-4 | 6-5 | 6-6 |
| Controlled pH | Not controlled | | pH 2 (± 10%) | | pH 6 (± 10%) | | pH 3 (± 10%) | | pH 4 (± 10%) | | pH 5 (± 10%) | |
| API: TM agent | 1:4 | 1:250 | 1:4 | 1:250 | 1:4 | 1:250 | 1:4 | 1:250 | 1:4 | 1:250 | 1:4 | 1:250 |
| Varenicline Tartrate | 0.85 (0.5 mg as varenicline) | | | | | | | | | | | |
| Beta-Cyclodextrin | 2 | 125 | 2 | 125 | 2 | 125 | 2 | 125 | 2 | 125 | 2 | 125 |
| Excipients (%) | | | | | | | | | | | | |
| Mannitol | 30.0 | | | | | | | | | | | |
| Avicell | 10.0 | | | | | | | | | | | |
| HPC-L | 3.0 | | | | | | | | | | | |
| Magnesium stearate | 0.5 | | | | | | | | | | | |
| Sucralose | 2.0 | | | | | | | | | | | |
| Peppermint powder | 2.0 | | | | | | | | | | | |
| pH control agent (Tartaric acid) | q.s. | | | | | | | | | | | |
| Water | q.s. | | | | | | | | | | | |

| | | Comparative Example | | | | | | Examples No. | | | | | |
|---|---|---|---|---|---|---|---|---|---|---|---|---|---|
| | | 6-1 | 6-2 | 6-3 | 6-4 | 6-5 | 6-6 | 6-1 | 6-2 | 6-3 | 6-4 | 6-5 | 6-6 |
| Evaluation parameter | Weigh | Score = Each parameter value × Weigh | | | | | | | | | | | |
| Effect of taste masking | 3 | 9 | 9 | 9 | 9 | 9 | 9 | 12 | 12 | 12 | 12 | 12 | 12 |
| Hardness | 1 | 4 | 4 | 4 | 4 | 4 | 4 | 4 | 4 | 4 | 4 | 4 | 4 |
| Total score | | 13 | 13 | 13 | 13 | 13 | 13 | 16 | 16 | 16 | 16 | 16 | 16 |

TABLE 17

| | Comparative Example | | | | | | Examples (mg/mL) | | | | | |
|---|---|---|---|---|---|---|---|---|---|---|---|---|
| | 6-7 | 6-8 | 6-9 | 6-10 | 6-11 | 6-12 | 6-7 | 6-8 | 6-9 | 6-10 | 6-11 | 6-12 |
| Controlled pH | Not controlled | | pH 2 (± 10%) | | pH 6 (± 10%) | | pH 3 (± 10%) | | pH 4 (± 10%) | | pH 5 (± 10%) | |
| API: TM agent | 1:4 | 1:250 | 1:4 | 1:250 | 1:4 | 1:250 | 1:4 | 1:250 | 1:4 | 1:250 | 1:4 | 1:250 |
| Varenicline Tartrate | 0.82 (0.5 mg as varenicline) | | | | | | | | | | | |
| Beta-Cyclodextrin | 2 | 125 | 2 | 125 | 2 | 125 | 2 | 125 | 2 | 125 | 2 | 125 |
| Excipients (%) | | | | | | | | | | | | |
| Mannitol | 30.0 | | | | | | | | | | | |
| Avicell | 10.0 | | | | | | | | | | | |
| HPC-L | 3.0 | | | | | | | | | | | |
| Magnesium stearate | 0.5 | | | | | | | | | | | |
| Sucralose | 2.0 | | | | | | | | | | | |
| Peppermint powder | 2.0 | | | | | | | | | | | |
| pH control agent (Tartaric acid) | q.s. | | | | | | | | | | | |
| Water | q.s. | | | | | | | | | | | |

| | | Comparative Example | | | | | | Examples No. | | | | | |
|---|---|---|---|---|---|---|---|---|---|---|---|---|---|
| | | 6-7 | 6-8 | 6-9 | 6-10 | 6-11 | 6-12 | 6-7 | 6-8 | 6-9 | 6-10 | 6-11 | 6-12 |
| Evaluation parameter | Weigh | Score = Each parameter value × Weigh | | | | | | | | | | | |
| Effect of taste masking | 3 | 9 | 9 | 9 | 9 | 9 | 9 | 12 | 12 | 12 | 12 | 12 | 12 |
| Hardness | 1 | 4 | 4 | 4 | 4 | 4 | 4 | 4 | 4 | 4 | 4 | 4 | 4 |
| Total score | | 13 | 13 | 13 | 13 | 13 | 13 | 16 | 16 | 16 | 16 | 16 | 16 |

Example 6. Effect of Acid Addition on Stabilization

Test Example

Stability Test Method

Assay (%) and total impurities (%) were investigated by HPLC (high-performance liquid chromatography). A test solution for conducting HPLC was prepared as follows.

Preparation of Test Solution

A film containing 1 mg of a varenicline salt was put in a 10-mL flask and mixed with a mobile phase. The mixture was centrifuged for 20 minutes. The centrifugate was filtered through a 0.45-μm filter (water-soluble PVDF). As a result, a test solution (0.1 mg/mL) was obtained.

Preparation of Standard Solution 20 mg of a varenicline salt was added to a 200-mL flask together with a mobile phase. The mixture was sonicated and then stirred. As a result, a standard solution (0.1 mg/mL) was obtained.

HPLC Condition

Detector: UV (237 nm)
Column: ODS, 150×4.6 mm, 5 μm
Flow rate: 1.0 mL/min
Mobile Phase
A: ACN:buffer (88:12)
B: ACN
Buffer=1.3606 g of $KH_2PO_4$ dissolved in 1 L of distilled water.
<Gradient Condition>

TABLE 18

| Time (min) | Mobile phase A | Mobile phase B |
|---|---|---|
| 0 | 100 | 0 |
| 3 | 100 | 0 |
| 15 | 80 | 20 |
| 58 | 35 | 65 |
| 60 | 100 | 0 |
| 70 | 100 | 0 |

Assay (%)

$$\text{Assay (\%)} = A_t/A_s \times C_s/C_t \times P$$

$A_t$: area response of varenicline in test sample solution
$A_s$: area response of varenicline in standard sample solution
$C_t$: varenicline concentration of test sample solution
$C_s$: varenicline concentration of standard sample solution
P: purity of desmopressin acetate standard (%)

Total Impurities (%)

Total impurities=sum total of individual impurities

Individual impurity (%)=$A_i/A_t \times 100$ $A_i$: area response of impurity in test sample solution
$A_t$: area response of varenicline in test sample solution LOD (Loss on Drying)

LOD was tested according to the method described in USP 731 at 105° C. for 4 hours.

The assay and impurity evaluation criteria were as follows.

TABLE 19

| | Change amount |
|---|---|
| Assay judgement | |
| Very good | ≤±0.5% |
| Good | −0.5% to −1.0% |
| Bad | −1.0% to −2.0% |
| Poor | ≥−5.0% |
| Impurity judgement | |
| Very good | ≤0.3% |
| Good | 0.3% to 0.6% |
| Bad | 0.6% to 1.0% |
| Poor | ≥1.0% |

Stability was tested under an accelerated condition (40±2° C., relative humidity 60±5%). In order to prevent contact with external water, the test was conducted after putting the pharmaceutical formulation in a multi-layered aluminum foil container and sealing the same.

The assay (%) is the amount of varenicline retained in the pharmaceutical formulation and change amount (%) is the change of the assay (%) value depending on time, reflecting the change in the amount of varenicline in the pharmaceutical formulation with time. The assay (%) was measured 0, 4 and 8 weeks later and the difference between the assay (%) at week 0 and the assay (%) at week 8 was recorded as the change amount (%).

The total impurities (%) is the amount of varenicline-derived related substances in the pharmaceutical formulation and the change amount (%) is the change of the total impurities (%) value depending on time, reflecting the change in the amount of the varenicline related substances in the pharmaceutical formulation with time. The total impurities (%) was measured at weeks 0, 4 and 8 and the difference between the total impurities (%) at week 0 and the total impurities (%) at week 8 was recorded as the change amount (%).

6-1. Effect of Organic Acid on Stabilization of Film Formulation Containing Varenicline Tartrate The stability of a varenicline salt was investigated after adjusting the pH of the solution for preparing a film formulation to 4 using different organic acids.

Preparation method: After dissolving varenicline tartrate and β-cyclodextrin in water, the mixture was stirred for 1 hour while heating to 60-70° C. Then, after adding glycerin, sucralose, a sweetener and a flavor, the mixture was dissolved by stirring and then homogenized using a homogenizer (Ultra-Turrax T-24, IKA). Then, after adding pullulan and homogenizing using the same homogenizer, a diluted acidifier solution (tartaric acid 5 mg/mL) was added to the solution for preparing a film little by little until the pH described in Tables 20 and 21 was reached. After removing a gas from the solution in vacuo, the solution was coated on a PET film to an appropriate thickness. Then, a film formulation containing varenicline tartrate was prepared by drying the same at 60-80° C.

TABLE 20

| | Comparative Example | Examples | | | | | | | |
|---|---|---|---|---|---|---|---|---|---|
| | 7-1 | 7-1 | 7-2 | 7-3 | 7-4 | 7-5 | 7-6 | 7-7 | 7-8 |
| Varenicline Tartrate | | | | | 1.00 | | | | |
| Beta-Cyclodextrin | | | | | 50.00 | | | | |
| Citric acid | — | Add until pH 4.0 | — | — | — | — | — | — | — |
| Tartaric acid | — | — | Add until pH 4.0 | — | — | — | — | — | — |
| Salicylic acid | — | — | — | Add until pH 4.0 | — | — | — | — | — |
| Benzoic acid | — | — | — | — | Add until pH 4.0 | — | — | — | — |
| Acetic acid | — | — | — | — | — | Add until pH 4.0 | — | — | — |
| Phosphoric acid | — | — | — | — | — | — | Add until pH 4.0 | — | — |
| pyruvic acid | — | — | — | — | — | — | — | Add until pH 4.0 | — |
| Gallic acid | — | — | — | — | — | — | — | — | Add until pH 4.0 |
| Excipients (%) | | | | | | | | | |
| Pullulan | | | | | 50.00 | | | | |
| Glycerin | | | | | 8.00 | | | | |
| TiO$_2$ | | | | | 10.00 | | | | |
| Sucralose | | | | | 3.000 | | | | |
| Ferric oxide (red) | | | | | q.s. | | | | |
| Peppermint powder | | | | | q.s. | | | | |
| Water | | | | | q.s. | | | | |
| LOD (%) | 9.1 | 9.8 | 10.1 | 9.3 | 9.6 | 9.8 | 9.5 | 9.8 | 9.7 |

LOD test condition: 105° C., 4 hrs.

TABLE 21

| Contents | Period (weeks) | Ref 7-1 | Examples | | | | | | | |
|---|---|---|---|---|---|---|---|---|---|---|
| | | | 7-1 | 7-2 | 7-3 | 7-4 | 7-5 | 7-6 | 7-7 | 7-8 |
| Assay (%) | 0 | 100.4 | 100.9 | 100.4 | 100.6 | 101.3 | 100.7 | 101.6 | 100.9 | 100.7 |
| | 4 | 95.4 | 100.7 | 100.3 | 100.5 | 101.4 | 100.5 | 101.4 | 100.7 | 100.6 |
| | 8 | 95.1 | 100.7 | 100.2 | 100.8 | 101.3 | 100.6 | 101.5 | 100.7 | 100.5 |
| Change amount (%) | | −5.3 | −0.2 | −0.2 | 0.2 | 0.0 | −0.1 | −0.1 | −0.2 | −0.2 |
| Judgement | | Poor | Very Good | Very good | Very good | Very good | Very good | Very good | Very good | Very good |
| Total impurity (%) | 0 | ≤0.1 | ≤0.1 | ≤0.1 | ≤0.1 | ≤0.1 | ≤0.1 | ≤0.1 | ≤0.1 | ≤0.1 |
| | 4 | ≤1.5 | ≤0.2 | ≤0.2 | ≤0.2 | ≤0.2 | ≤0.2 | ≤0.2 | ≤0.3 | ≤0.3 |
| | 8 | ≤1.9 | ≤0.5 | ≤0.2 | ≤0.2 | ≤0.2 | ≤0.2 | ≤0.2 | ≤0.5 | ≤0.5 |
| Change amount (%) | | 1.8 | 0.4 | 0.1 | 0.1 | 0.1 | 0.1 | 0.1 | 0.4 | 0.4 |
| Judgement | | Poor | Good | Very good | Very good | Very good | Very good | Very good | Good | Good |

- Storage condition: Accelerated condition (40° C., 60% RH)
- Storage container: Multi-layer aluminum foil The change in the contents of varenicline and related substances depending on the organic acids added could be confirmed. In particular, the films prepared at pH 4.0 by adding tartaric acid, salicylic acid, benzoic acid, acetic acid or phosphoric acid showed superior stability with decreased change in varenicline content and less generation of related substance with time.

In addition, it was confirmed that the taste-masking effect was excellent and the solubility was higher when tartaric acid was added.

6-2. Effect of Organic Acid on Stabilization of Film Formulation Containing Varenicline Salicylate The stability of a varenicline salt was investigated after adjusting the pH of the solution for preparing a film formulation to 4 using different organic acids.

TABLE 22

| | Examples (mg/unit) | | | | | | | | |
|---|---|---|---|---|---|---|---|---|---|
| | 7-2 | 7-9 | 7-10 | 7-11 | 7-12 | 7-13 | 7-14 | 7-15 | 7-16 |
| Ingredients | Ref. | | | | | | | | |
| Varenicline Salicylate | | | | | 1.00 | | | | |
| Beta-Cyclodextrin | | | | | 50.00 | | | | |
| Citric acid | — | Add until pH 4.0 | — | — | — | — | — | — | — |
| Tartaric acid | — | — | Add until pH 4.0 | — | — | — | — | — | — |
| Salicylic acid | — | — | — | Add until pH 4.0 | — | — | — | — | — |
| Benzoic acid | — | — | — | — | Add until pH 4.0 | — | — | — | — |
| Acetic acid | — | — | — | — | — | Add until pH 4.0 | — | — | — |
| Phosphoric acid | — | — | — | — | — | — | Add until pH 4.0 | — | — |
| Pyruvic acid | — | — | — | — | — | — | — | Add until pH 4.0 | — |
| Gallic acid | — | — | — | — | — | — | — | — | Add until pH 4.0 |
| Excipients (%) | | | | | | | | | |
| Pullulan | | | | | 50.00 | | | | |
| Glycerin | | | | | 8.00 | | | | |
| TiO$_2$ | | | | | 10.00 | | | | |
| Sucralose | | | | | 3.000 | | | | |
| Ferric oxide (red) | | | | | q.s. | | | | |
| Peppermint powder | | | | | q.s. | | | | |
| Water | | | | | q.s. | | | | |
| LOD (%) | 9.3 | 9.4 | 9.6 | 9.4 | 9.5 | 9.8 | 9.9 | 9.5 | 9.6 |

TABLE 23

| | | Examples | | | | | | | | |
|---|---|---|---|---|---|---|---|---|---|---|
| Contents | Period (weeks) | Ref 7-2 | 7-9 | 7-10 | 7-11 | 7-12 | 7-13 | 7-14 | 7-15 | 7-16 |
| Assay (%) | 0 | 100.4 | 100.9 | 100.3 | 100.5 | 101.4 | 100.6 | 101.4 | 100.8 | 100.8 |
| | 4 | 95.5 | 100.8 | 100.2 | 100.4 | 101.2 | 100.6 | 101.7 | 100.6 | 100.5 |
| | 8 | 95.7 | 100.6 | 100.5 | 100.6 | 101.4 | 100.7 | 101.2 | 100.5 | 100.6 |
| Change amount (%) | | −4.7 | −0.3 | 0.2 | 0.1 | 0.0 | 0.1 | −0.2 | −0.3 | −0.2 |
| Judgement | | Poor | Very Good | Very good | Very good | Very good | Very good | Very good | Very good | Very good |
| Total impurity (%) | 0 | ≤0.1 | ≤0.1 | ≤0.1 | ≤0.1 | ≤0.1 | ≤0.1 | ≤0.1 | ≤0.1 | ≤0.1 |
| | 4 | ≤1.5 | ≤0.2 | ≤0.2 | ≤0.2 | ≤0.2 | ≤0.2 | ≤0.2 | ≤0.3 | ≤0.3 |
| | 8 | ≤20 | ≤0.5 | ≤0.2 | ≤0.2 | ≤0.2 | ≤0.2 | ≤0.2 | ≤0.5 | ≤0.5 |
| Change amount (%) | | 1.9 | 0.4 | 0.1 | 0.1 | 0.1 | 0.1 | 0.1 | 0.4 | 0.4 |
| Judgement | | Poor | Good | Very good | Very good | Very good | Very good | Very good | Good | Good |

Storage condition: Accelerated condition (40° C., 60% RH)
Storage container: multi-layered aluminum foil The change in the contents of varenicline and related substances depending on the organic acids added could be confirmed. In particular, the films prepared at pH 4.0 by adding tartaric acid, salicylic acid, benzoic acid, acetic acid or phosphoric acid showed superior stability with decreased change in varenicline content and less generation of related substance with time.

6-3. Effect of pH on Stabilization of Film Formulation Containing Varenicline Tartrate

TABLE 24

| Ingredients | 8-1 Ref | 8-1 | 8-2 | 8-3 | 8-4 | 8-5 | 8-6 | 8-7 | 8-8 | 8-9 | 8-10 | 8-11 | 8-12 |
|---|---|---|---|---|---|---|---|---|---|---|---|---|---|
| | | Adjust pH 3.0 (± 10%) | | | Adjust pH 4.0 (± 10%) | | | Adjust pH 5.0 (± 10%) | | | Adjust pH 6.0 (± 10%) | | |
| Varenicline Tartrate | | | | | | | 1.00 | | | | | | |
| Beta-Cyclodextrin | | | | | | | 50.00 | | | | | | |
| Tartaric acid | — | ○ | — | — | — | — | — | — | — | — | — | — | — |
| | — | — | — | — | ○ | — | — | — | — | — | — | — | — |
| | — | — | — | — | — | — | — | ○ | — | — | — | — | — |
| | — | — | — | — | — | — | — | — | — | — | ○ | — | — |
| Salicylic acid | — | — | ○ | — | — | — | — | — | — | — | — | — | — |
| | — | — | — | — | — | ○ | — | — | — | — | — | — | — |
| | — | — | — | — | — | — | — | — | ○ | — | — | — | — |
| | — | — | — | — | — | — | — | — | — | — | — | ○ | — |
| Acetic acid | — | — | — | ○ | — | — | — | — | — | — | — | — | — |
| | — | — | — | — | — | — | ○ | — | — | — | — | — | — |
| | — | — | — | — | — | — | — | — | — | ○ | — | — | — |
| | — | — | — | — | — | — | — | — | — | — | — | — | ○ |

Excipients (%)

| | |
|---|---|
| Pullulan | 50.00 |
| Glycerin | 8.00 |
| TiO$_2$ | 5.00 |
| Sucralose | 0.10 |
| Ferric oxide (red) | 0.30 |
| Peppermint powder | q.s. |
| Flavor | q.s. |
| Water | q.s. |

| LOD (%) | 9.5 | 9.4 | 9.6 | 9.5 | 9.8 | 9.9 | 9.4 | 9.5 | 9.3 | 9.6 | 10.1 | 9.5 | 9.8 |

TABLE 25

| Contents | Period (weeks) | Ref. 8-1 | 8-1 | 8-2 | 8-3 | 8-4 | 8-5 | 8-6 | 8-7 | 8-8 | 8-9 | 8-10 | 8-11 | 8-12 |
|---|---|---|---|---|---|---|---|---|---|---|---|---|---|---|
| Assay (%) | 0 | 100.4 | 100.7 | 100.3 | 100.3 | 101.4 | 100.7 | 101.6 | 101.2 | 100.7 | 101.3 | 101.4 | 100.9 | 100.9 |
| | 4 | 95.4 | 100.5 | 100.1 | 100.2 | 101.3 | 100.6 | 101.3 | 101.1 | 100.6 | 101.1 | 100.5 | 100.3 | 100.2 |
| | 8 | 95.1 | 100.3 | 100.4 | 100.1 | 101.2 | 100.5 | 101.2 | 100.9 | 100.8 | 100.9 | 99.8 | 99.5 | 99.8 |
| Change amount (%) | | −5.3 | −0.4 | 0.1 | −0.2 | −0.2 | −0.2 | −0.4 | −0.3 | 0.1 | −0.4 | −1.6 | −1.4 | −1.1 |
| Judgement | | Poor | Very good | Very good | Very good | Very good | Very good | Very good | Very good | Very good | Very good | bad | bad | bad |
| Total impurity (%) | 0 | ≤0.1 | ≤0.1 | ≤0.1 | ≤0.1 | ≤0.1 | ≤0.1 | ≤0.1 | ≤0.1 | ≤0.1 | ≤0.1 | 0.1 | 0.1 | 0.1 |
| | 4 | ≤1.2 | ≤0.2 | ≤0.2 | ≤0.2 | ≤0.2 | ≤0.2 | ≤0.2 | ≤0.2 | ≤0.2 | ≤0.2 | 1.0 | 1.0 | 1.0 |
| | 8 | ≤1.9 | ≤0.3 | ≤0.3 | ≤0.3 | ≤0.3 | ≤0.3 | ≤0.3 | ≤0.3 | ≤0.3 | ≤0.3 | 1.3 | 1.6 | 1.7 |
| Change amount (%) | | 1.8 | 0.2 | 0.2 | 0.2 | 0.2 | 0.2 | 0.2 | 0.2 | 0.2 | 0.2 | 1.2 | 1.5 | 1.6 |
| Judgement | | Poor | Very good | Very good | Very good | Very good | Very good | Very good | Very good | Very good | Very good | poor | poor | poor |

It was confirmed that superior stability with less change in varenicline content and less generation of related substances was achieved when the pH of the solution for preparing a film was 3-5.

6-4. Effect of pH on Stabilization of Film Formulation Containing Varenicline Salicylate

TABLE 26

| Ingredients | 9-1 Ref | 9-1 | 9-2 | 9-3 | 9-4 | 9-5 | 9-6 | 9-7 | 9-8 | 9-9 | 9-10 | 9-11 | 9-12 |
|---|---|---|---|---|---|---|---|---|---|---|---|---|---|
| | | Adjust pH 3.0 (± 10%) | | | Adjust pH 4.0 (± 10%) | | | Adjust pH 5.0 (± 10%) | | | Adjust pH 6.0 (± 10%) | | |
| Varenicline Salicylate | | | | | | 1.00 | | | | | | | |
| Beta-Cyclodextrin | | | | | | 50.00 | | | | | | | |
| Tartaric acid | — | ○ | — | — | — | — | — | — | — | — | — | — | — |
| | — | — | — | — | ○ | — | — | — | — | — | — | — | — |
| | — | — | — | — | — | — | — | ○ | — | — | — | — | — |
| | — | — | — | — | — | — | — | — | — | — | ○ | — | — |
| Salicylic acid | — | — | ○ | — | — | — | — | — | — | — | — | — | — |
| | — | — | — | — | — | ○ | — | — | — | — | — | — | — |
| | — | — | — | — | — | — | — | — | ○ | — | — | — | — |
| | — | — | — | — | — | — | — | — | — | — | — | ○ | — |
| Acetic acid | — | — | — | ○ | — | — | — | — | — | — | — | — | — |
| | — | — | — | — | — | — | ○ | — | — | — | — | — | — |
| | — | — | — | — | — | — | — | — | — | ○ | — | — | — |
| | — | — | — | — | — | — | — | — | — | — | — | — | ○ |
| Excipients (%) | | | | | | | | | | | | | |
| Pullulan | | | | | | 50.00 | | | | | | | |
| Glycerin | | | | | | 8.00 | | | | | | | |
| TiO$_2$ | | | | | | 5.00 | | | | | | | |
| Sucralose | | | | | | 0.10 | | | | | | | |
| Ferric oxide (red) | | | | | | 0.30 | | | | | | | |
| Peppermint powder | | | | | | q.s. | | | | | | | |
| Flavor | | | | | | q.s. | | | | | | | |
| Water | | | | | | q.s. | | | | | | | |
| LOD (%) | 9.6 | 9.4 | 9.5 | 9.3 | 9.6 | 9.7 | 9.4 | 9.1 | 9.8 | 9.6 | 9.4 | 9.5 | 9.6 |

TABLE 27

| Contents | Period (weeks) | Examples | | | | | | | | | | | | |
|---|---|---|---|---|---|---|---|---|---|---|---|---|---|
| | | 9-1 | 9-1 | 9-2 | 9-3 | 9-4 | 9-5 | 9-6 | 9-7 | 9-8 | 9-9 | 9-10 | 9-11 | 9-12 |
| Assay (%) | 0 | 100.4 | 100.6 | 100.4 | 100.2 | 101.5 | 100.5 | 101.4 | 101.5 | 100.6 | 101.3 | 101.3 | 100.9 | 100.8 |
| | 4 | 95.4 | 100.3 | 100.3 | 100.6 | 101.4 | 100.4 | 101.3 | 101.4 | 100.4 | 101 | 100.7 | 100.4 | 100.1 |
| | 8 | 95.1 | 100.4 | 100.4 | 100.4 | 101.5 | 100.5 | 101.6 | 101.2 | 100.4 | 100.9 | 99.7 | 99.6 | 99.7 |
| Change amount (%) | | −5.3 | −0.2 | 0.0 | 0.2 | 0.0 | 0.0 | 0.2 | −0.3 | −0.2 | −0.4 | −1.6 | −1.3 | −1.1 |
| Judgement | | Poor | Very good | Very good | Very good | Very good | Very good | Very good | Very good | Very good | Very good | bad | bad | bad |
| Total impurity (%) | 0 | ≤0.1 | ≤0.1 | ≤0.1 | ≤0.1 | ≤0.1 | ≤0.1 | ≤0.1 | ≤0.1 | ≤0.1 | ≤0.1 | ≤0.1 | ≤0.1 | ≤0.1 |
| | 4 | ≤1.2 | ≤0.2 | ≤0.2 | ≤0.2 | ≤0.2 | ≤0.2 | ≤0.2 | ≤0.2 | ≤0.2 | ≤0.2 | ≤1.0 | ≤1.0 | ≤1.0 |
| | 8 | ≤1.9 | ≤0.3 | ≤0.3 | ≤0.3 | ≤0.3 | ≤0.3 | ≤0.3 | ≤0.3 | ≤0.3 | ≤0.3 | ≤1.4 | ≤1.5 | ≤1.6 |
| Change amount (%) | | 1.8 | 0.2 | 0.2 | 0.2 | 0.2 | 0.2 | 0.2 | 0.2 | 0.2 | 0.2 | 1.3 | 1.4 | 1.5 |
| Judgement | | Poor | Very good | Very good | Very good | Very good | Very good | Very good | Very good | Very good | Very good | poor | poor | poor |

It was confirmed that superior stability with less change in varenicline content and less generation of related substances was achieved when the pH of the solution for preparing a film was 3-5.

INDUSTRIAL APPLICABILITY

A formulation the present disclosure is a superior orally administered formulation which masks the bitter taste of varenicline or a pharmaceutically acceptable salt thereof and improves swallowing.

The formulation the present disclosure may be used as a smoking cessation aid.

What is claimed is:

1. An orally administered pharmaceutical formulation, comprising an inclusion complex formed as varenicline salicylate included in cyclodextrin,
    wherein the formulation further comprises one or more acids selected from the group consisting of tartaric acid, salicylic acid, benzoic acid, acetic acid, and phosphoric acid,
    wherein the pharmaceutical formulation is prepared by a method comprising
        (S1) a step of preparing a mixture of varenicline salicylate and a solvent;
        (S2) a step of forming a mixture comprising a cyclodextrin inclusion complex by adding cyclodextrin to the mixture and forming a cyclodextrin inclusion complex by heating and stirring the same;
        (S3) a step of preparing solution for preparing a formulation by mixing a pharmaceutically acceptable additive in the mixture comprising the cyclodextrin inclusion complex; and
        (S4) a step of preparing the solution for preparing a formulation into the formulation,
            wherein, in step (S2), the cyclodextrin inclusion complex is formed by using an acid during the stirring and the inclusion complex of the varenicline salicylate and the cyclodextrin is formed at pH 2.5 to 5.5 by adding the acid, and
            wherein the acid is one or more acids selected from the group consisting of tartaric acid, salicylic acid, benzoic acid, acetic acid, and phosphoric acid.

2. The orally administered pharmaceutical formulation according to claim 1, wherein the cyclodextrin is β-cyclodextrin.

3. The orally administered pharmaceutical formulation according to claim 1, wherein the formulation is a film formulation comprising the varenicline salicylate and the cyclodextrin at a weight ratio of 2:1 to 1:230 (varenicline salicylate: cyclodextrin).

4. The orally administered pharmaceutical formulation according to claim 1, wherein the formulation is a rapidly disintegrating tablet comprising the varenicline salicylate and the cyclodextrin at a weight ratio of 1:4 to 1:520 (varenicline salicylate: cyclodextrin).

5. The orally administered pharmaceutical formulation according to claim 1, wherein the formulation masks the bitter taste of the varenicline salicylate and exhibits improved stability of the drug in the formulation.

6. The orally administered pharmaceutical formulation according to claim 1, wherein the formulation is an orally dissolving film or a disintegrating tablet, wherein 80% or more of the disintegrating tablet dissolves, disperses, or disintegrates within 10 minutes after oral administration.

7. A method for preparing an orally administered formulation of varenicline salicylate, comprising:
    (S1) a step of preparing a mixture of varenicline salicylate and a solvent;
    (S2) a step of forming a mixture comprising a cyclodextrin inclusion complex by adding cyclodextrin to the mixture and forming a cyclodextrin inclusion complex by heating and stirring the same;
    (S3) a step of preparing solution for preparing a formulation by mixing a pharmaceutically acceptable additive in the mixture comprising the cyclodextrin inclusion complex; and
    (S4) a step of preparing the solution for preparing a formulation into the formulation,
    wherein, in step (S2), the cyclodextrin inclusion complex is formed by using an acid during the stirring and the inclusion complex of the varenicline salicylate and the cyclodextrin is formed at pH 2.5 to 5.5 by adding the acid, and
    wherein the acid is one or more acids selected from the group consisting of tartaric acid, salicylic acid, benzoic acid, acetic acid, and phosphoric acid.

8. The method for preparing a formulation according to claim 7, wherein the cyclodextrin is β-cyclodextrin.

9. The method for preparing a formulation according to claim 7, wherein the formulation is an orally administered film and, in the step (S4), the film is prepared by homogenizing a film-forming polymer and the mixture of the inclusion complex and the pharmaceutically acceptable additive and then drying the same.

10. The method for preparing a formulation according to claim 7, wherein, in the step (S2), the inclusion complex of the varenicline salicylate and the cyclodextrin is formed by mixing the varenicline salicylate and the cyclodextrin at a weight ratio of 2:1 to 1:230 (varenicline or pharmaceutically acceptable salt thereof: cyclodextrin) at pH 2.5-5.5 by adding the acid.

11. A smoking cessation aid, comprising an inclusion complex wherein varenicline salicylate is included in cyclodextrin, which is prepared by the preparation method according to claim 7.

* * * * *